United States Patent [19]

Saperstein

[11] Patent Number: 5,026,638

[45] Date of Patent: Jun. 25, 1991

[54] ANTIBIOTIC SENSITIVITY TEST FOR PATHOGENIC ORGANISMS PRESENT IN MASTITIC MILK

[76] Inventor: George Saperstein, R.F.D. #1, Box 127, Pomfret Center, Conn. 06259

[21] Appl. No.: 224,613

[22] Filed: Jul. 27, 1988

[51] Int. Cl.$^5$ .......................... C12Q 1/18; C12Q 1/02; C12N 1/00
[52] U.S. Cl. ...................................... 435/32; 435/29; 435/30; 435/33; 435/243; 435/252.1; 435/252.4; 435/252.8
[58] Field of Search ...................... 435/29, 30, 32, 33, 435/243, 252.1, 252.4, 252.8, 253.4, 253.6

[56] References Cited

U.S. PATENT DOCUMENTS

| | | | |
|---|---|---|---|
| 3,664,306 | 5/1972 | Quayle et al. | 119/14.14 |
| 3,713,985 | 1/1973 | Astle | 195/103.5 R |
| 3,728,228 | 4/1973 | Duranty | 195/127 |
| 3,742,194 | 6/1973 | Caruso et al. | 235/92 PC |
| 3,762,371 | 10/1973 | Quayle et al. | 119/14.14 |
| 3,772,154 | 11/1973 | Isenberg et al. | 195/103.5 R |
| 3,806,424 | 4/1974 | Rolinson | 195/127 |
| 3,826,717 | 7/1974 | Gilbert et al. | 195/103.5 R |
| 3,832,532 | 8/1974 | Praglin et al. | 235/151.3 |
| 3,925,166 | 12/1975 | Blume | 195/139 |
| 3,937,655 | 2/1976 | Pfeiffer et al. | 195/103.5 R |
| 3,957,583 | 5/1976 | Gibson et al. | 195/103.5 R |
| 3,968,774 | 7/1976 | Massie | 119/14.14 |
| 3,986,534 | 10/1976 | Schmidt | 141/1 |
| 3,992,265 | 11/1976 | Hansen | 195/127 |
| 4,014,745 | 3/1977 | Fletcher et al. | 195/103.5 K |
| 4,070,248 | 1/1978 | Schmidt | 195/103.5 K |
| 4,077,845 | 4/1977 | Johnson | 195/103.5 K |
| 4,132,599 | 1/1979 | Picciolo et al. | 195/103.5 K |
| 4,153,512 | 5/1979 | Messner et al. | 195/103.5 R |
| 4,311,794 | 1/1982 | Melnick et al. | 435/32 |
| 4,340,671 | 7/1982 | Gibson | 435/32 |
| 4,376,053 | 3/1983 | Bullock et al. | 210/767 |
| 4,385,590 | 5/1983 | Mortensen | 119/14.01 |
| 4,448,534 | 5/1984 | Wertz et al. | 356/435 |
| 4,643,968 | 2/1987 | Weaver | 435/32 |
| 4,659,656 | 4/1987 | Sandholm | 435/7 |

FOREIGN PATENT DOCUMENTS 0039763 3/1980 Japan .
0840736 6/1981 U.S.S.R. .

OTHER PUBLICATIONS

Sogaard, H., Biological Abstract, vol. 76, No. 5, Abstract No. 31925 (1983).
Adetosoye, A. I. et al., Biological Abstracts, vol. 68, No. 7, Abstract No. 42047 (1979).
Kostrzynski, S. et al., Biological Abstracts, vol. 85, No. 5, Abstract No. 45063 (1988).
Hussain et al., Biological Abstracts, vol. 79, No. 11, Abstract No. 96436 (1985).

Primary Examiner—Esther L. Kepplinger
Assistant Examiner—Toni R. Scheiner
Attorney, Agent, or Firm—Sughrue, Mion, Zinn, Macpeak & Seas

[57] ABSTRACT

The present invention relates to a method for determining the antibiotic sensitivity of pathogenic microorganisms present in milk obtained from mammals afflicted with mastitis, an apparatus for use with the same and an antibiotic sensitivity test kit containing the same.

21 Claims, 1 Drawing Sheet

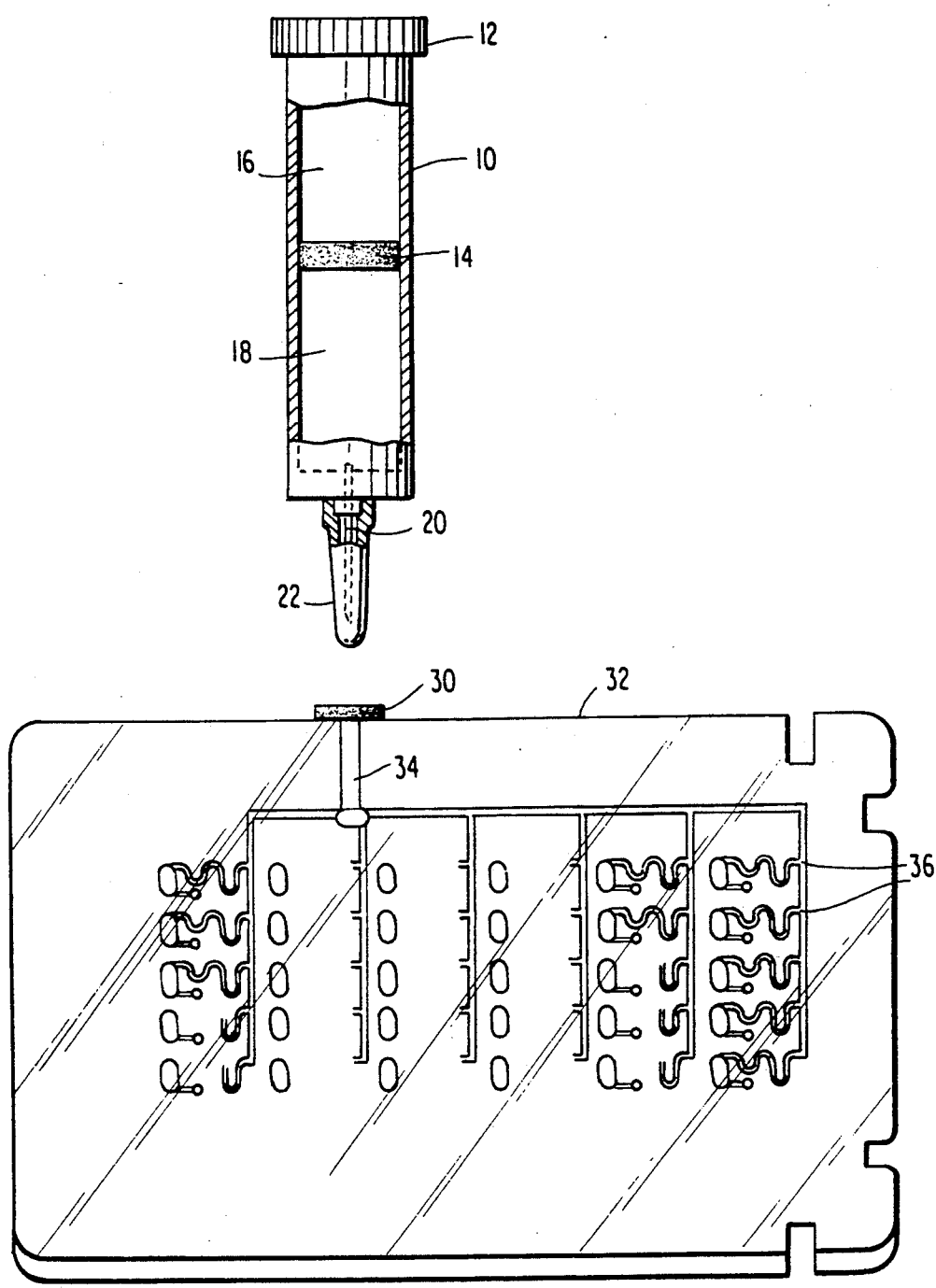

ANTIBIOTIC SENSITIVITY TEST FOR PATHOGENIC ORGANISMS PRESENT IN MASTITIC MILK

FIELD OF THE INVENTION

The present invention relates to a method for determining the antibiotic sensitivity of pathogenic microorganisms present in milk obtained from mammals afflicted with mastitis, an apparatus for use with the same and an antibiotic sensitivity test kit containing the same.

BACKGROUND OF THE INVENTION

Mastitis is the most common and most costly disease of dairy animals in the world. Mastitis is diagnosed by observing heat, swelling, redness, pain and abnormal milk in the affected gland. Most dairy farmers treat this disease with antibiotics. Treatment is usually instituted immediately upon diagnosis of the disease. The antibiotic chosen for treatment is based upon past experience with what has been working pure guess work or the results of an antibiotic sensitivity test.

Farmers generally do not submit milk samples for antibiotic sensitivity tests because of the unacceptable lag time between the submission of milk samples and the receipt of the test results. That is, by the time the antibiotic sensitivity test results are reported to the farmer, i.e., 48 hours to 1 week, most cases of mastitis have either cleared up or progressed to a much greater severity. Some animals may even lose function of the affected quarter while others may die from septicemia. Thus antibiotic sensitivity tests are not generally employed.

The two types of antibiotic sensitivity tests which are currently employed are the disc sensitivity test (Bauer. A. W. et al, *Am. J. Chem. Path.*, 45:493 (1966)) and the broth or agar dilution antibiotic susceptibility test (National Committee for Clinical Laboratory Standards. Vol. 5. No. 22 (1985)). To date, the disc sensitivity test is the most commonly employed antibiotic sensitivity test for mastitis.

In the disc sensitivity test, milk, collected using sterile techniques, is streaked out on a blood agar plate. Then, pathogenic microorganisms, i.e., *Staphlococcus aureus, Streptococcus agalactiae Streptococcus dysgalactiae, Streptococcus uberis, Escherichia coli* and *Klebsiella species*, which account for over 90% of bovine mastitis pathogens, are isolated after 12 to 24 hours of incubation on the blood agar plate. After isolation, a standard amount of the microorganisms, sometimes diluted in trypticase soy broth, is streaked on a Mueller Hinton agar plate and allowed to grow, thereby forming a carpet of microorganisms after 18 to 24 hours. Then, discs, which have previously been impregnated with various antibiotics, are placed in the plate. If the antibiotic is effective against the particular type of microorganism present. a ring or zone of inhibition appears on the plate. A sliding scale is used to measure how strongly the antibiotic inhibits the bacterial growth.

The disc sensitivity test is disadvantageous not only because of the length of time required to run the test, i.e., 36 to 48 hours but, also, because sometimes there is a poor correlation between the in vitro results and the in vivo response to a particular antibiotic. This is believed to be due to the fact that antibiotics behave differently in milk than in agar (*Laboratory and Field Handbook on Bovine Mastitis*, Eds. Research Committee of National Mastitis Council, National Mastitis Council Inc., Arlington, Va. (1987): and Owens, W. E. et al *J. Dairy Sci.,* 70:1946 (1987)). In addition the disc sensitivity test is less accurate than the broth or agar dilution antibiotic sensitivity test (Turck M. et al. *Ann. Int. Med.,* 58:56 (1963)).

The broth or agar dilution antibiotic sensitivity test, in its miniaturized form, is believed to more closely predict the effect of an antibiotic in vivo because it uses specific concentrations of antibiotics that correlate with known serum concentrations necessary to be effective against a mastitis causing microorganism infection. In spite of this, due to the expense, availability and lack of veterinary antibiotic panels, this test is rarely performed on milk.

In the broth or agar dilution antibiotic sensitivity test, a known quantity of microorganisms, usually isolated on a blood agar plate from the original sample, is placed in wells of a microtiter plate, a series of tubes or a commercially available cassette consisting of many wells. The quantity of microorganisms is measured by adding the microorganisms to culture medium until the turbidity matches that of a standard, i.e. the MacFarland Standard. The greater the turbidity the more microorganisms are present. The MacFarland Standard is employed because if there are not enough microorganisms, some wells will not receive any microorganisms and no growth would give false results. Further if too many microorganisms are present, they might overgrow and overwhelm the antibiotic, again giving false results.

The wells of the microtiter plate the series of test tubes or the commercially available cassette to which the microorganism-culture medium mixture is added, contain serial dilutions of various antibiotics. After 6 to 16 hours of incubation the wells, test tubes or cassette are observed for turbidity. High turbidity indicates growth and means the microorganisms are resistant to the antibiotic at that level. Low turbidity means the microorganisms are sensitive to the antibiotic at that level. Low turbidity in a well, test tube or cassette having a low concentration of antibiotic indicates high sensitivity. Antibiotic concentration can be correlated with serum levels achieved using typical therapeutic dosages. Thus, this test is more quantitative than the disc sensitivity test.

However, the broth or agar dilution antibiotic sensitivity test is disadvantageous not only because of the length of time required to run the test, i.e., 18 to 40 hours but, also, because this test is not carried out on the original sample of milk. i.e.. the original sample of milk is first cultured and the microorganisms identified. Further this test is carried out in a culture medium or laboratory broth rather than in milk. Antibiotics behave differently in milk than in culture media (*Laboratory and Field Handbook on Bovine Mastitis,* Eds. Research Committee of National Mastitis Council, National Mastitis Council, Inc., Arlington, Va. (1987): and Owens, W. E. et al, *J. Dairy Sci.,* 70:1946 (1987)). In addition the currently available test procedure is too difficult and expensive to run in a veterinarian's office or on a farm.

Thus, to date, a cost effective, fast, and accurate test for determining the antibiotic sensitivity of the major pathogenic microorganisms present in milk obtained from mammals afflicted with mastitis has not been developed (*Laboratory and Field Handbook on Bovine Mastitis,* Eds. Research Committee of National Mastitis Council, National Mastitis Council, Inc., Arlington, Va. (1987)). Moreover, the method of the present invention is unique in that it tests for antibiotic sensitivity without the need for first identifying the microorganism.

The fermentation of lactose to lactic acid is common to many microorganisms. This fact is used by microbiologists as an aid in the identification of microorganisms. That is, an unknown microorganism is either a lactose fermenter or it is not.

The Hotis test, developed in 1936 (Hotis, R. P. et al, U.S. Dept. Agr. Cir. 400 (1936)), takes advantage of lactose fermentation and the use of a pH color indicator in an attempt to screen milk samples for the presence of *Streptococcus aqalactiae* (*Bovine Mastitis*, Schalm, O. W. et al, Lea Febiger, Philadelphia (1971), particularly pages 150–164). The purpose of the Hotis test is only to identify the presence of *Streptococcus agalactiae* in the cow.

The Hotis test is not applicable to the method of the present invention because it is not an antibiotic sensitivity test. Further, the Hotis test is disadvantageous because it is generally not accurate in clinical cases of mastitis (*Bovine Mastitis*, Schalm, O. W. et al, Lea Febiger, Philadelphia (1971), particularly pages 150–164).

SUMMARY OF THE INVENTION

Accordingly, an object of the present invention is to provide a cost effective, fast, and accurate test for determining the antibiotic sensitivity of the major pathogenic bacteria present in milk obtained from mammals afflicted with mastitis without the need for first identifying the microorganism(s).

Another object of the present invention is to provide an apparatus for use in carrying out the antibiotic sensitivity test.

Still another object of the present invention is to provide an antibiotic sensitivity test kit containing the apparatus.

These and other objects of the present invention will be apparent from the detailed description of the present invention provided hereinafter.

In one embodiment, the above-described objects of the present invention have been met by a method for determining the antibiotic sensitivity of pathogenic microorganisms present in milk obtained from a mammal afflicted with mastitis comprising the steps of:
(A) collecting a sample of milk from a mammal afflicted with mastitis:
(B) admixing the resulting collected sample of milk of step (A) with sterilized milk and incubating the resulting mixture at about 34° to 38° C. for about 2 to 12 hours so as to obtain a culture of said microorganisms in the milk admixture:
(C) admixing the resulting culture of step (B) or an aliquot thereof, with an antibiotic and incubating at about 34° to 38° C. for about 4 to 24 hours: and
(D) determining the antibiotic sensitivity of the resulting antibiotic containing culture of step (C) by measuring the pH of said antibiotic containing culture, whereby a culture which is more acidic than the culture of step (B) indicates that said pathogenic microorganisms are not sensitive to said antibiotic.

In another embodiment, the above-described objects of the present invention have been met by an antibiotic sensitivity test kit comprising:
(A) a sample mixing container comprising:
(i) a tube;
(ii) a means for dividing the tube into upper and lower chambers, said upper chamber for receiving a collected sample of milk to be tested, said lower chamber for receiving reagents for treating said collected sample of milk and said means is capable of removing clots and foreign material from said collected sample of milk;
(iii) a hollow needle coupled to said lower chamber; and
(iv) a means for sealing said upper chamber; and
(B) a multi-specimen test card, wherein said multi-specimen test card contains at least one antibiotic therein at at least one concentration.

BRIEF DESCRIPTION OF THE DRAWING

The Figure illustrates a preferred embodiment of the antibiotic sensitivity test kit of the present invention.

DETAILED DESCRIPTION OF THE INVENTION

I. The Method

As discussed above, in one embodiment, the above objects of the present invention have been met by a method for determining the antibiotic sensitivity of pathogenic microorganisms present in milk obtained from a mammal afflicted with mastitis comprising the steps of:
(A) collecting a sample of milk from a mammal afflicted with mastitis;
(B) admixing the resulting collected sample of milk of step (A) with sterilized milk and incubating the resulting mixture at about 34° to 38° C. for about 2 to 12 hours so as to obtain a culture of said microorganism in the milk admixture;
(C) admixing the resulting culture of step (B) or an aliquot thereof, with an antibiotic and incubating at about 34° to 38° C. for about 4 to 24 hours; and
(D) determining the antibiotic sensitivity of the resulting antibiotic containing culture of step (C) by measuring the pH of said antibiotic containing culture, whereby a culture which is more acidic than the culture of step (B) indicates that said pathogenic microorganisms are not sensitive to said antibiotic.

The particular mammals afflicted with mastitis from which the sample of milk is collected is not critical to the present invention. Examples of such mammals include cows, goats, sheep, humans, dogs, cats, horses, asses, pigs, bison, water buffalos, rabbits, rats, mice, guinea pigs, yaks, camels and whales. Preferred mammals include cows, goats, sheep, humans, horses, water buffalos, yaks and camels. These mammals are preferred in terms of commercial milk production and, in the case of humans, in terms of public health.

The collected sample of milk obtained from the mammal is typically a stripping of milk which contains about 1.0 to 5.0 ml of fluid depending upon the size of the teat and the degree of inflammation.

The particular sterilized milk employed in the present invention is not critical thereto. Examples of such sterilized milk include sterilized skim milk, sterilized low fat milk or sterilized whole milk. Sterilized skim milk is preferred because it is the most stable and miscible.

The particular source of the sterilized milk is not critical to the present invention. Examples of such sources include the mammals set forth above. However, it is preferred, for a closer correlation of the results to the in vivo situation, that the source of the sterilized milk be the same mammalian species from which the collected sample of milk for testing is obtained.

The particular mode of sterilizing the milk is not critical to the present invention. That is, the milk can be sterilized by means of, e.g., heat, radiation or filtration. The use of heat is preferred because it is simple, inexpensive and safe.

Sterilized milk is employed in the present invention as culture broth. Further, such is employed in the present invention in order to offset the alkaline secretions in the infected mammal, thereby bringing the pH of the collected sample of milk to about neutral. Sterilized milk is also employed in the present invention in order to provide sufficient lactose for the microorganisms to ferment to lactic acid, thereby turning the sample acidic.

The mixing ratio of the collected sample of milk to sterilized milk is not critical to the present invention. Generally, the mixing ratio of the collected sample of milk to sterilized milk is from about 90:10 to 10:90 parts by volume, preferably from about 40:60 to 60:40 parts by volume.

The admixture of the collected sample of milk and sterilized milk is incubated at about 34° to 38° C., preferably about 35° to 37° C. for about 2 to 12 hours, preferably about 2 to 3 hours, so as to obtain a culture of pathogenic microorganisms in the milk admixture.

The particular pathogenic microorganisms which are contained in the milk are not critical to the present invention and can be any lactose fermenting pathogenic microorganism associated with mastitis or a combination thereof. Examples of such microorganisms include *Staphlococcus aureus, Streptococcus agalactiae, Streptococcus dysgalactiae, Streptococcus uberis, Escherichia coli* and *Klebsiella species.* As discussed above, these microorganisms account for over 90% of all cases of mastitis in bovines and all are lactic acid producing microorganisms.

Other more rare mastitis causing microorganisms which have been isolated from bovine milk and which are lactose fermenters include *Streptococcus faecalis, Streptococcus zooepidemicus,* Group G *Streptococci, Staphlococcus epidermidis, Enterobacter species, Corynebacterium pyogenes, Clostridium perfrinoens, Actinobacillus lignieresi, Fusobacterium necrophorum, Diplococcus pneumoniae* and *Listeria monocytogenes.*

Mastitis causing microorganisms which ferment lactose and which have been isolated from sheep milk include *Staphlococcus aureus, Actinobacillus lionieresi, Escherichia coli, Streptococcus uberis, Streptococcus dysgalactiae* and *Streptococcus agalactiae.*

Mastitis causing microorganisms which ferment lactose and which have been isolated from goat milk include *Streptococcus aqalactiae, Streptococcus dysgalactiae, Streptococcus pyogenes, Staphlococcus aureus* and *Staphlococcus epidermidis.*

Mastitis causing microorganisms which ferment lactose and which have been isolated from pig milk include *Aerobacter aerogenes, Escherichia coli, Klebsiella species, Staphlococci, Streptococcus agalactiae, Streptococcus dysgalactiae* and *Streptococcus uberis.*

A mastitis causing microorganism which ferments lactose and which has been from horse milk is *Streptococcus zooepidemicus.*

The culture of microorganisms, or aliquot thereof (generally about 0.01 to 1.0 ml, preferably about 0.02 to 0.2 ml). is incubated with an antibiotic at about 34° to 38° C. preferably about 35° to 37° C. for about 4 to 24 hours, preferably about 6 to 10 hours, with or without agitation.

The antibiotic sensitivity of the resulting antibiotic containing culture is measured by measuring the pH of the antibiotic containing culture. The pH of the antibiotic containing culture can be measured using any means to measure pH. Examples of such means for measuring pH include litmus paper, a pH meter or a pH color indicator. The use of a pH color indicator is preferred in terms of ease of carrying out the method of the present invention.

When a pH color indicator is employed, the pH color indicator is admixed with the collected sample of milk and the sterilized milk in steps (B) or (C). The pH is observed by visually observing the color of the antibiotic containing culture.

The particular pH color indicator employed in the present invention is not critical thereto. Examples of such pH color indicators include bromcresol purple, thymol blue, phenol red, litmus and neutral red. The preferred pH color indicator is bromcresol purple because the pH range at which it changes color makes it the most sensitive of these pH color indicators.

The amount of pH color indicator employed is not critical to the present invention. Generally, the pH color indicator is employed in an amount of from about 0.4 to 1.6 mg/ml of admixture of collected sample of milk and sterilized milk, preferably about 0.6 to 1.0 mg/ml of admixture of collected sample of milk and sterilized milk.

The particular antibiotic employed in the present invention is not critical thereto. Examples of such antibiotics include ampicillin, cephalothin, novobiocin, gentamicin, oxytetracycline, penicillin, trimethoprim-sulfa, streptomycin, erythromycin, oxacillin and tylosin. Preferred examples of such antibiotics include ampicillin, cephalothin, novobiocin, oxytetracycline, penicillin, streptomycin, erythromycin, oxacillin and tylosin because they are or have been approved by the U.S. Food and Drug Administration for use in dairy cows.

The amount of antibiotic employed is not critical to the present invention. Generally, the amount of antibiotic employed is from about 0.05 to about 100 µg/ml. preferably from about 0.1 to 65 µg/ml.

In a preferred embodiment of the present invention, the following step (E) is employed:
(E) simultaneously or subsequently repeating steps (C) and (D) with a different concentration of the antibiotic or with a different antibiotic at the same or different concentration in order to obtain an antibiotic sensitivity profile.

In a particularly preferred embodiment, a growth inhibitor of non-pathogenic microorganisms present in the collected sample of milk is admixed with the collected sample of milk and the sterilized milk so as to inhibit the growth of the non-pathogenic microorganisms present in the milk but not the growth of the pathogenic microorganisms present in the milk.

The particular growth inhibitor of non-pathogenic microorganisms present in the collected sample of milk is not critical to the present invention. Examples of such growth inhibitors include sodium azide, brilliant green, thallium acetate and dextrose.

The amount of growth inhibitor of non-pathogenic microorganisms present in the collected sample of milk employed is not critical to the present invention. Generally, the ratio of growth inhibitor of non-pathogenic microorganisms present in the collected sample of milk to the admixture of collected sample of milk and sterilized milk is from about 1:1000 to 1:50,000 parts by weight per parts by volume, preferably from about 1:15,000 to 1:20,000 parts by weight per parts by volume.

Using the method of the present invention, it is not necessary to first isolate and identify the particular microorganisms causing the mastitis as in the disc sensitivity test and broth or agar dilution antibiotic sensitivity test. Further, by using milk as a culture broth instead of a laboratory culture broth or media, the antibiotic sensitivity results using the method of the present invention are closer to what naturally occurs in vivo. In addition, by using milk as a culture broth, the method of the present invention is accurate in clinical cases of mastitis whereas the Hotis test is generally not accurate in clinical cases of mastitis. Preferably, by observing color change-no color change, as an indication of antibiotic resistance or sensitivity, the antibiotic sensitivity test of the present invention can be conducted in a veterinarian's office or even on a farm. Neither a laboratory nor expensive equipment are necessary to carry out the method of the present invention.

Furthermore, there is no need in the method of the present invention for standardizing the innoculum to the MacFarland Standard as in the broth or agar dilution antibiotic sensitivity test. This is because the method of the present invention does not measure turbidity but, rather, pH. In addition, since mastitis causing microorganisms grow rapidly in milk and the collected sample of milk is preincubated in sterilized milk for about 2 hours in the method of the present invention, there is generally enough microorganisms to fill the test wells. Microorganism overgrowth is not a problem in the method of the present invention either because in the case of innoculating the wells with excessive numbers of microorganisms, much more rapid growth occurs in wells with ineffective antibiotics than in wells with effective antibiotics, resulting in a more pronounced change in pH.

II. The Test Kit

As discussed above, in another embodiment, the above-described objects of the present invention have been met by an antibiotic sensitivity test kit comprising:
(A) a sample mixing container comprising:
 (i) a tube;
 (ii) a means for dividing the tube into upper and lower chambers, said upper chamber for receiving a collected sample of milk to be tested, said lower chamber for receiving reagents for treating said collected sample of milk and said means is capable of removing clots and foreign material from said collected sample of milk;
 (iii) a hollow needle coupled to said lower chamber; and
 (iv) a means for sealing said upper chamber; and
(B) a multi-specimen test card, wherein said multi-specimen test card contains at least one antibiotic therein at at least one concentration.

The particular material comprising the tube is not critical to the present invention as long as such is not toxic to microorganisms. For example, the tube may be of plastic, metal or glass. Plastic is the preferred material because it is the least expensive and easiest to manufacture.

The particular material comprising the means for removing clots or foreign material, such as a filter, is not critical to the present invention. The filter may be of plastic, metal, paper, cotton, or synthetic fabric. Plastic is again the preferred material because it is the least expensive and easiest to manufacture.

The pore size of the filter is not critical to the present invention and generally is about 1.0 to 1000 $\mu$, preferably about 100 to 500 $\mu$.

The means for sealing the upper chamber is not critical to the present invention. For example, means for sealing the upper chamber include a screw cap or a rubber stopper. A screw cap is preferred because it is the easiest way to maintain sterility while collecting the sample of milk.

If desired, a means for sealing the hollow needle can also be provided on the sample mixing chamber.

The means for sealing the hollow needle is not critical to the present invention. For example, the means for sealing the hollow needle include a cap, a plug or a rubber stopper. A cap is preferred because it can be easily removed and replaced for safety and will preserve the sterility of the system.

The hollow needle is preferably a double ended needle.

The multi-specimen test card may be an open system or a closed system, preferably a closed system because microbial contamination during storage and use is minimized with such a system.

As an open system, the multi-specimen test card may be a microtiter test plate or a rack of test tubes.

As a closed system, the multi-specimen test card may be a Vitek TM card (U.S. Pat. No. 3,957,583) or other cassettes as described in U.S. Pat. Nos. 3,713,985; 3,826,717; 3,832,532; 3,992,265; 4,070,248; 4,077,845; 4,153,512; and 4,448,534.

As a closed system, the multi-specimen test card preferably comprises:
 (i') an injection port;
 (ii') a series of evacuated test wells each containing the same or different antibiotic at the same or different concentrations, wherein all of the wells are in fluid communication with said injection port; and
 (iii') a septum for sealing said injection port,
wherein said septum is puncturable by said hollow needle so as to transfer the resulting treated sample of milk into said test wells.

A particularly preferred example of the multi-specimen test card of the closed system type is The Vitek TM card manufactured by VITEK Systems, Hazelwood, Mo. A Vitek TM card 32, as shown in the Figure, is the preferred multi-specimen test card because it is a closed system with one injection port 34° to fill all of the wells 36 which contain various antibiotics at various concentrations. Since the Vitek TM card is commercially available, it is described and illustrated without exactly detailing all of the components thereof. The card is modified in accordance with this invention to be capped with a septum once it is evacuated.

Each antibiotic is employed in to 1 to 5, preferably 3, wells of the multi-specimen test card at increasing concentrations with the middle well being an estimate of the concentration of antibiotic which is expected to be achieved in milk when an animal is treated with a commercially available intramammary antibiotic preparation.

Using the multi-specimen test card, it is possible to determine which one of, e.g., two antibiotics, to which the mastitis causing microorganisms in the cow are found to be sensitive, is the best antibiotic to be chosen for treatment of the mastitis. That is, the multi-specimen test card allows one to directly compare the effectiveness of different antibiotics at different concentrations.

Preferred antibiotics and concentrations employed in the multi-specimen test card are shown in Table 1 below.

TABLE 1

| Antibiotic | Well Number and Concentration of Antibiotic | | |
|---|---|---|---|
| Ampicillin | 1 | 2 | 3 |
| | 2.50 | 10.0 | 20.0 |
| Penicillin | 4 | 5 | 6 |
| | 1.25 | 5.0 | 10.0 |
| Cephalothin | 7 | 8 | 9 |
| | 6.25 | 25.0 | 50.0 |
| Streptomycin | 10 | 11 | 12 |
| | 2.50 | 10.0 | 20.0 |
| Erythromycin | 13 | 14 | 15 |
| | 5.00 | 20.0 | 40.0 |
| Cloxacillin (oxacillin) | 16 | 17 | 18 |
| | 3.75 | 15.0 | 30.0 |
| Oxytetracycline | 19 | 20 | 21 |
| | 7.50 | 30.0 | 60.0 |
| Novobiocin | 22 | 23 | 24 |
| | 2.50 | 10.0 | 20.0 |
| None (control) | 25 | | |
| | 0.00 | | |

The numbers in the boxes indicate the micrograms of antibiotic precoated in each well.

Each antibiotic is employed in 3 wells of increasing concentrations as listed in Table 1 above with the middle well being the estimated concentration of antibiotic which is expected to be achieved in milk when an animal is treated with one tube of a commercially available U.S. Food and Drug Administration approved intramammary antibiotic preparation. As shown in Table 1 above, the first well contains one-fourth the concentration of antibiotic as the middle well and the third well contains twice the concentration of antibiotic as the middle well.

Examples of commercially available U.S. Food and Drug Administration approved intramammary antibiotic preparations include those set forth in Table 2 below.

TABLE 2

| Generic Drug Name | Trade Name of Intramammary Infusion | Manufacturer |
|---|---|---|
| Hetacillin (metabolized to Ampicillin) | Hetacin ®-K | Fort Dodge Laboratories, Inc. Fort Dodge, IA |
| Cephalothin | Cefa-Lak ® | Fort Dodge Laboratories, Inc. Fort Dodge, IA |
| Erythromycin | Erythro ®-36 | Ceva Laboratories Overland Park, KS |
| Penicillin | Special Formula 17900-Forte ™ | Upjohn Company Kalamazoo, MI |
| Novobiocin | Special Formula 17900-Forte ™ | Upjohn Company Kalamazoo, MI |
| Streptomycin | Quartermaster ™ Suspension | Upjohn Company Kalamazoo, MI |
| Oxytetracycline | Liquamast ® | Pfizer Inc. New York, NY |
| Cloxacillin | Dariclox ® | Beecham Labs. Bristol, TN |

In the open system, the antibiotics can be added before, after or along with the addition of the resulting treated sample of milk. In the closed system, the antibiotics are generally already contained in the multi-specimen test card prior to the addition of the resulting treated sample of milk.

In a preferred embodiment, as illustrated in the Figure, the sample mixing chamber of the present invention comprises a tube 10 with a screw cap 12 on top, a filter 14 which divides the tube into an upper chamber 16 and a lower chamber 18 and a capped double ended needle 20 extending from the bottom of the tube. Sterilized milk, a pH color indicator and a growth inhibitor are placed in the lower chamber 18. The collected sample of milk is placed in the upper chamber 16 by loading in the open end with the screw cap removed. The collected sample of milk filters through the filter 14 dividing the upper and lower chambers by means of gravity to remove clots and flakes in the collected sample of milk. The sample mixing chamber is then incubated. Next, after removing the cap 22 of the double ended needle 20, the double ended needle is inserted into the septum 30 added to a Vitek ™ card 32. Since most of the air from the Vitek ™ card has been removed, the vacuum in the card facilitates the transfer of the resulting treated sample of milk through the injection port 34 into the wells 36. The card is then incubated. Next, color changes or lack thereof are visually observed indicating growth or no growth, i.e., no antibiotic sensitivity or antibiotic sensitivity, respectively.

When reading the test, the ideal antibiotic(s) chosen for treatment is the one(s) where no growth occurred in any of the wells. A good second choice is one where growth occurred only in the low concentration well. If growth occurred in the first 2 wells, the microorganism is intermediate in its sensitivity to the antibiotic. Thus, the antibiotic may be effective at higher than usual dosages. If growth occurred in all 3 wells of the same antibiotic, this indicates that the microorganism causing the mastitis in the particular mammal is resistant to the antibiotic.

The antibiotic sensitivity test kit preferably also contains an incubator for incubating the cultures in the sample mixing chamber of the present invention and/or a pH color indicator reference chart.

The following example is provided for illustrative purposes only and is in no way intended to limit the scope of the present invention.

EXAMPLE

After discarding the first stripping of milk, the tip of a teat to be sampled was washed with a disinfectant, such as ethanol, so as to make sure there was no residual dirt or environmental microorganisms at the end of the teat. After air drying the teat, the second stripping was squirted into the upper chamber of the sample mixing chamber of the present invention. It is important to maintain sterility. Further, both the teat and the apparatus should be held at a 45° angle to avoid getting dirt from the animal into the sample mixing chamber. This procedure is a standard milk sampling protocol.

The cap of the sample mixing chamber was then immediately replaced. The coarse filter in the middle of the tube filtered out the clots and flakes and allowed the fluid part of the milk (containing the mastitis causing microorganisms) to mix with about 2.0 ml of sterilized milk present in the lower chamber. The sterilized milk contained about 0.2 ml of a solution comprising 390 ml of water. 3.0 g sodium azide, and 8.0 g of bromcresol purple dissolved in 100 ml of ethanol. After 2 hours of incubation at 35° to 37° C. the cap of the double ended needle was removed and the double ended needle placed through the rubber stopper on a Vitek TM card injection port. (The Vitek TM card was modified by sealing the injection port with a rubber stopper and evacuating most of the air therefrom.) The rubber stopper on the Vitek TM card may have a peel off sticker to preserve sterility. Vacuum drew the milk into the Vitek TM card and filled all of the wells. The card was then placed in an incubator and read for color changes after 4 to 10 hours.

The Vitek TM card contained the antibiotics in the various concentrations listed in Table 3 below. The surplus mixture remaining in the sample mixing container was kept at room temperature as a negative control indicating the original color (blue). i.e., essentially no growth. The well which did not contain antibiotics was the positive control and showed the color change resulting from maximum microorganism growth (green to yellow). The antibiotic sensitivity test results obtained for four individual mastitis afflicted cows infected with four different mastitis causing microorganisms are shown in Table 3 below.

TABLE 3

Antibiotic Sensitivity Test Results After 11-12 Hours Incubation at 37° C.
Resistance (R) or Sensitivity (S)

| Antibiotic | Concentration ($\mu$g/ml) | Cow A (Klebsiella species infection*) | Cow B (Staphlococcus aureus infection*) | Cow C (Streptococcus dysgalactiae infection*) | Cow D (Streptococcus uberis infection*) |
|---|---|---|---|---|---|
| Chloramphenicol | 2 | R | S | S | R |
| Chloramphenicol | 8 | S | S | S | S |
| Tetracycline | 2 | R | S | R | R |
| Tetracycline | 8 | R | S | S | R |
| Tetracycline | 32 | S | S | S | R |
| Carbenicillin | 32 | R | S | S | S |
| Carbenicillin | 128 | R | S | S | S |
| Gentamicin | 0.5 | R | R | R | R |
| Gentamicin | 2 | R | S | R | R |
| Gentamicin | 8 | S | S | S | R |
| Cefamandole | 2 | R | S | S | S |
| Cefamandole | 16 | R | S | S | S |
| Cefamandole | 128 | S | S | S | S |
| Tobramycin | 0.5 | R | R | R | R |
| Tobramycin | 2 | R | S | S | R |
| Tobramycin | 8 | R | S | S | R |
| Amikacin | 2 | R | R | R | R |
| Amikacin | 8 | R | S | R | R |
| Amikacin | 32 | S | S | S | R |
| Cefoxitin | 2 | R | S | S | S |
| Cefoxitin | 16 | R | S | S | S |
| Cefoxitin | 128 | S | S | S | S |
| Cephalothin | 2 | R | S | S | S |
| Cephalothin | 16 | R | S | S | S |
| Trimethoprim-sulfamethoxazole | 20 | S | S | S | R |
| Trimethoprim-sulfamethoxazole | 40 | S | S | S | R |
| Ampicillin | 0.5 | R | R | S | S |
| Ampicillin | 4 | R | R | S | S |
| Ampicillin | 32 | R | R | S | S |

*Organisms were identified independently

A comparison of the results obtained using the method of the present invention and the disc sensitivity test (DST) on individual cows diagnosed as having mastitis is shown in Table 4 below.

TABLE 4

Comparison of Antibiotic Sensitivity Test Results
Resistance (R) or Sensitivity (S)

| | | Ampicillin ($\mu$g/ml) | Cephalothin ($\mu$g/ml) | Tetracycline ($\mu$g/ml) | Gentamicin ($\mu$g/ml) | Chloramphenicol ($\mu$g/ml) |
|---|---|---|---|---|---|---|
| Cow A [1] (Klebsiella species infection) | Invention (12 hrs) [2] | R (4) | R (16) | S (32) | S (8) | S (8) |
| | DST | R (10) | S (30) [3] | S (30) | S (10) | S (30) |
| Cow B [4] (Staphlococcus aureus infection) | Invention (12 hrs) | R (4) | S (16) | S (32) | S (8) | S (8) |
| | DST | R (10) | S (30) | S (30) | S (10) | S (30) |
| Cow C [4] | Invention (11 hrs) | S (4) | S (16) | S (32) | S (8) | S (8) |

TABLE 4-continued

| | | Comparison of Antibiotic Sensitivity Test Results Resistance (R) or Sensitivity (S) | | | | |
|---|---|---|---|---|---|---|
| | | Ampicillin (μg/ml) | Cephalothin (μg/ml) | Tetracycline (μg/ml) | Gentamicin (μg/ml) | Chloramphenicol (μg/ml) |
| (Streptococcus dysgalactiae infection) | DST | S (10) | S (30) | R (30) | S (10) | S (30) |
| Cow D [4] | Invention (11 hrs) | S (4) | S (16) | R (32) | R (8) | S (8) |
| (Streptococcus uberis infection) | DST | S (10) | S (30) | S (30) | S (10) | S (30) |

[1] Cow A responded to treatment with sulfa drugs and oxytetracycline by clinical recovery but lost function of the gland. This is a typical response to Klebsiella infection.
[2] Incubation time
[3] The farmer used this antibiotic and found it ineffective in treating the mastitis infection.
[4] Cows B, C and D responded to treatment with cephalothin.

As shown in Table 4 above, in four actual cases of mastitis (representing four major bovine mastitis causing pathogens). there was 90% (18 of 20 side-by-side comparative tests of antibiotic sensitivity) agreement at comparable concentrations between the test of the present invention and the disc sensitivity test. Furthermore, as shown by the lack of clinical response of cow A to cephalothin, it is probable that 10% disagreement represents the greater accuracy of the test of the present invention as compared to the disc sensitivity test.

While the invention has been described in detail and with reference to specific embodiments thereof, it will be apparent to one skilled in the art that various changes and modifications can be made therein without departing from the spirit and scope thereof.

I claim:

1. A method for determining the antibiotic sensitivity of pathogenic microorganisms present in milk obtained from a mammal afflicted with mastitis comprising the steps of:
   (A) collecting a sample of milk from a mammal afflicted with mastitis;
   (B) admixing the resulting collected sample of milk of step (A) with sterilized milk and incubating the resulting mixture at about 34° to 38° C. for about 2 to 12 hours so as to obtain a culture of said microorganisms in the milk admixture;
   (C) admixing the resulting culture of step (B) or an aliquot thereof, with an antibiotic and incubating at about 34° to 38° C. for about 4 to 24 hours; and
   (D) determining the antibiotic sensitivity of the resulting antibiotic containing culture of step (C) by measuring the pH of said antibiotic containing culture, whereby a culture which is more acidic than the original culture indicates that said pathogenic microorganisms are not sensitive to said antibiotic.

2. The method as claimed in claim 1, further comprising step (E):
   (E) simultaneously or subsequently repeating steps (C) and (D) with a different concentration of the antibiotic or with a different antibiotic at the same or different concentration in order to obtain an antibiotic sensitivity profile.

3. The method as claimed in claim 1, wherein said mammal is selected from the group consisting of cows, goats, sheep, humans, dogs, cats, horses, asses, pigs, bison, water buffalos, rabbits, rats, mice, guinea pigs, yaks, camels and whales.

4. The method as claimed in claim 1, wherein said sterilized milk is selected from the group consisting of sterilized skim milk, sterilized low fat milk and sterilized whole milk.

5. The method as claimed in claim 1, wherein the ratio of the collected sample of milk to sterilized milk is from about 90:10 to 10:90 parts by volume.

6. The method as claimed in claim 5, wherein the ratio of the collected sample of milk to sterilized milk is from about 40:60 to 60:40 parts by volume.

7. The method as claimed in claim 1, wherein said incubation in step (B) is carried out at about 35° to 37° C. for about 2 to 3 hours.

8. The method as claimed in claim 1, wherein said incubation in step (C) is carried out at about 35° to 37° C. for about 6 to 10 hours.

9. The method as claimed in claim 1, wherein said antibiotic is selected from the group consisting of ampicillin, cephalothin, novobiocin, gentamicin, oxytetracycline, penicillin, trimethoprim-sulfa, streptomycin, erythromycin, oxacillin and tylosin.

10. The method as claimed in claim 9, wherein said antibiotic is selected from the group consisting of ampicillin, cephalothin, novobiocin, oxytetracycline, penicillin, streptomycin, erythromycin, oxacillin and tylosin.

11. The method as claimed in claim 1, wherein said antibiotic is employed in an amount of from about 0.05 to 100 μg/ml.

12. The method as claimed in claim 11, wherein said antibiotic is employed in an amount of from about 0.1 to 65 μg/ml.

13. The method as claimed in claim 1, wherein in step (B) or step (C). a pH color indicator is also admixed and the pH in step (D) is measured by visually observing the change in color of said antibiotic containing culture.

14. The method as claimed in claim 13, wherein said pH color indicator is at least one member selected from the group consisting of bromcresol purple, thymol blue, phenol red, litmus and neutral red.

15. The method as claimed in claim 13, wherein the pH color indicator is employed in an amount of from about 0.4 to 1.6 mg/ml of admixture of collected sample of milk and sterilized milk.

16. The method as claimed in claim 15, wherein the pH color indicator is employed in an amount of from about 0.6 to 1.0 mg/ml of admixture of collected sample of milk and sterilized milk.

17. The method as claimed in claim 1, wherein in step (B). a growth inhibitor of non-pathogenic microorganisms present in the collected sample of milk is also admixed.

18. The method as claimed in claim 17, wherein said growth inhibitor of non-pathogenic microorganisms present in the collected sample of milk is at least one member selected from the group selected from sodium azide, brilliant green, thallium acetate and dextrose.

19. The method as claimed in claim 17, wherein the ratio of growth inhibitor to admixture of collected sample of milk and sterilized milk is from about 1:1000 to 1:50,000 parts by weight per parts by volume.

20. The method as claimed in claim 19, wherein the ratio of growth inhibitor to admixture of collected sample of milk and sterilized mil is from about 1:15,000 to 1:20,000 parts by weight per parts by volume.

21. The method as claimed in claim 1, wherein said pathogenic microorganisms are at least one member selected from the group consisting of *Staphlococcus aureus, Streptococcus agalactiae, Streptococcus dysgalactie, Streptococcus uberis, Escherichia coli* and *Klebsiella* species.

* * * * *